United States Patent [19]

Simpson

[11] Patent Number: 4,596,560
[45] Date of Patent: Jun. 24, 1986

[54] GASTRONOMY TUBE PROTECTOR

[76] Inventor: Mary Simpson, Rte. 3, Shepherdsville, Ky. 40165

[21] Appl. No.: 440,954

[22] Filed: May 18, 1983

[51] Int. Cl.⁴ ............................................. A61M 25/02
[52] U.S. Cl. ................................... 604/174; 604/337; 128/DIG. 26
[58] Field of Search ....................... 604/174, 179, 337; 128/DIG. 26, 1 R; 206/210, 363

[56] References Cited

U.S. PATENT DOCUMENTS

| | | | |
|---|---|---|---|
| 3,160,158 | 12/1964 | Rayhart | 128/179 |
| 3,362,407 | 1/1968 | Miller et al. | 604/337 |
| 4,040,427 | 8/1977 | Winnie | 128/DIG. 26 |
| 4,087,864 | 5/1978 | LaBove et al. | 604/174 X |

*Primary Examiner*—Stephen C. Pellegrino
*Attorney, Agent, or Firm*—Edward M. Steutermann

[57] ABSTRACT

A pocket device for retaining a gastronomy tube entering from the stomach of a patient including a band having opposite ends with cooperative fastener at the opposite ends so that the band can be place around the abdomen of the patient, a pocket member provided generally centrally located on the band and including pocket opening and closing device to provide access to the pocket where a slit is provided in the band intermediate the ends of the band so that the slit is located within the perimeter of and covered by the pocket so that the gastronomy tube placed in the stomach of the patient is received through the slit and can be stored in the pocket when not in use where access to the tube can be provided by means of the pocket opening and closing device to allow feeding.

7 Claims, 2 Drawing Figures

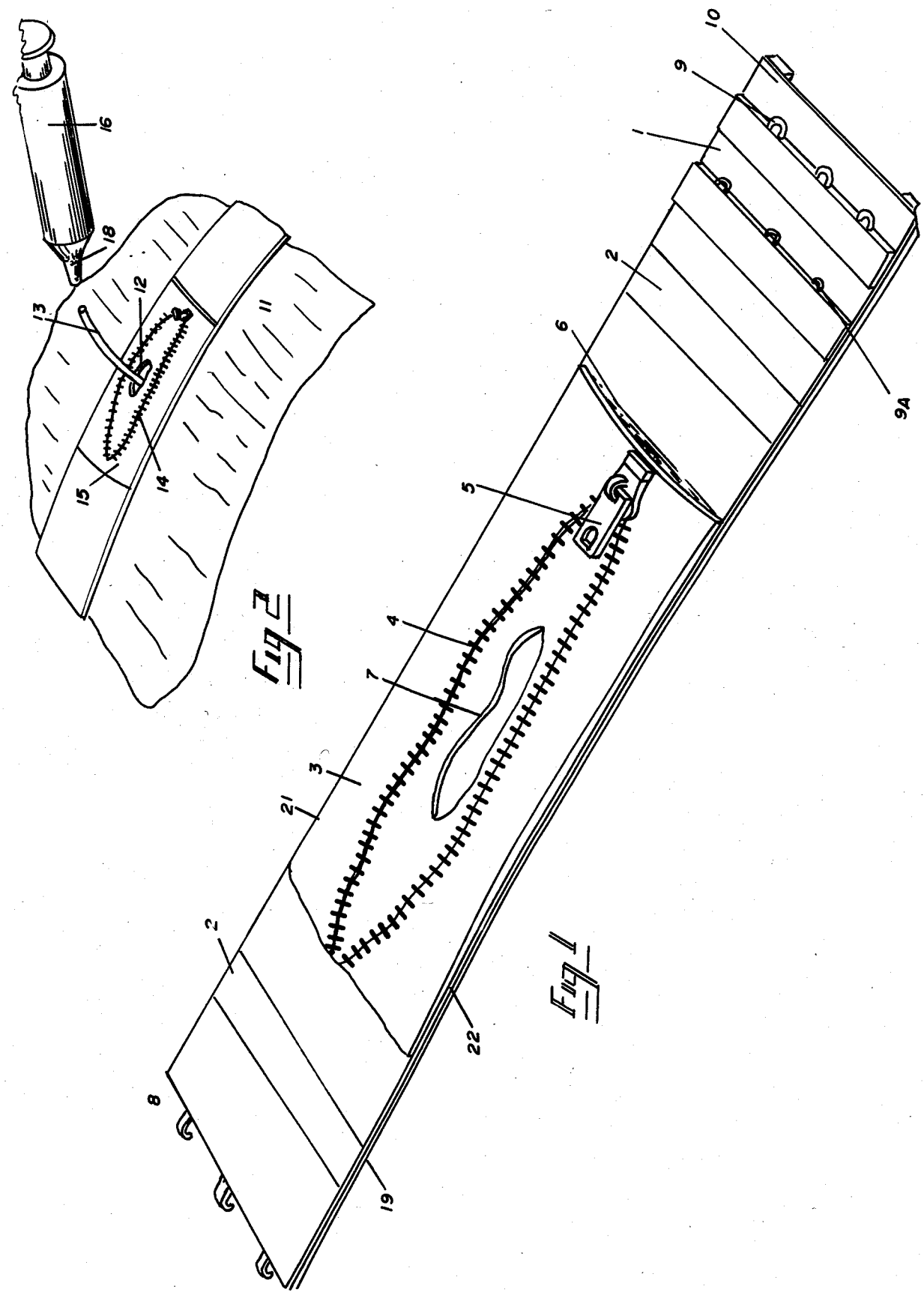

GASTRONOMY TUBE PROTECTOR

BACKGROUND OF THE INVENTION

The present invention relates to holding devices for gastronomy tubes. Gastronomy tubes are flexible, elongate tubes, usually of an elastomer, which are surgically inserted in the intestinal tract or stomach so that a free end of the tube protrudes outwardly from the abdomen of the patient.

The use of gastronomy tubes is required where intestinal difficulties or other problems are encountered in supplying food to the body and where food cannot be taken orally. In such instances, food is directly fed by means of the gastronomy tube into the intestines, usually by gravity or through a vial inserted in the end of the tube. The tube has normally been taped to the body at the opening of the stomach with the end of the tube dangling loosely. When feeding is necessary the tube is then located to receive the feeding mechanism which is connected to the tube to supply food into the stomach of the patient. However, when the patient is an infant or even a little older, the tube is irritating and either consciously or unconsciously the patient pulls at the loose end of the tube and frequently withdraws the tube from its point of insertion in the abdomenal wall. Also the exposed tube is subject to catching on objects. The resulting occurance is painful and requires immediate medical and surgical attention for reinsertion of the tube.

No prior art device is known to retain a gastronomy tube in place in a patient's stomach, and prevent accidental or intentional withdrawal or movement of the tube yet still provide the necessary access to the tube for feeding.

SUMMARY OF THE INVENTION

The present invention provides a new and useful arrangement for retaining and storing gastronomy tubes where the patient, and particularly a young patient, cannot easily tamper with the tube or remove it from the surgical incision. Further, devices within the scope of the present invention cannot be easily removed by a young child to frustrate the intent of the retaining device.

Moreover, devices within the scope of the present invention are economical to fabricate and easy to use, and the devices can be easily removed and washed frequently to maintain cleanliness and sanitary conditions around the point of insertion of the tube without damage to the tube insertion.

Additionally, devices within the scope of the present invention have been found to be very satisfactory in preventing the withdrawal of a gastronomy tube once inserted and to allow for the retention of the tube in a clean sanitary atmosphere to reduce the likelihood of infection or other unwanted problems.

Further, it has been found helpful to provide elastic strips along opposite sides of the band to prevent movement of the band along the abdomen of the user when the user is active.

It has been found, also, to further improve the device by making one edge of the band shorter edge is placed on the lower side of the abdomen to prevent movement of the band More particularly, the present invention provides a pocket device for retaining a gastronomy tube entering from the stomach of a patient including a band having opposite ends with cooperative fastener at the opposite ends so that the band can be place around the abdomen of the patient, a pocket member provided generally centrally located on the band and including pocket opening and closing device to provide access to the pocket where a slit is provided in the band intermediate the ends of the band so that the slit is located within the perimeter of and covered by the pocket so that the gastronomy tube placed in the stomach of the patient is received through the slit and can be stored in the pocket when not in use where access to the tube can be provided by means of the pocket opening and closing device to allow feeding.

An example within the scope of the present invention is illustrated within the accompanying drawing but it will be understood that various other arrangements also within the scope of the present invention will occur to those skilled in the art upon reading the disclosure set forth hereinafter.

BRIEF DESCRIPTION OF THE DRAWINGS

In one example in accordance with the present invention as shown in the illustrations,:

FIG. 1 is a perspective illustration of one of an arrangement within the scope of the present invention; and FIG. 2 is a perspective illustration of an arrangement as shown in FIG. 1 in actual use.

DETAILED DESCRIPTION OF THE DRAWINGS

Referring now to FIG. 1 the device includes a band 1 of selected length which can be elastic or where elastic sections 2 can be provided and spaced along the length of the band 1 to provide extension of the retraction of the band as the stomach fills and empties. A pocket 3 is formed intermediate the ends of the belt. A zipper 4 is provided to open and close the pocket. The pocket can be provided with gussets as at 6 to provide additional space within the pocket to facilitate retention of a tube as discussed hereinafter, although in some instances the pocket can consist of nothing more than an overlying layer of material with a zipper, such as zipper 4 with slit 5. In accordance with another feature of the present invention, a slit 7 is provided in band 1 within the perimeter of the pocket to allow entry of the tube. The pocket 3 can be of any selected size just so long as it is large enough to contain the tube (described hereinafter).

Further elastic bands 19 can be provided along the length of opposite sides 21, 22 of band 1 to prevent movement of band 1 along the abdomen of the user. Also side 22 can be longer than side 21 so that side 21 can be placed on the lower part of the abdomen to prevent the band from moving up the trunk of the user as the user moves.

Band 1 is wrapped around the body of the patient with the slit located in a position to receive the tube. Hooks 8, as shown, can be provided at one end of band 1 and positioned to engage eyelets 9 located in a row at the opposite end of the belt where an underlying section 10 can be provided to prevent the hooks 8 and eyelets 9 from contact the body of the patient. Also several rows of eyelets, for example a row of eyelets 9A can be provided to provide adjustable sizes within limits or so that the same size belt can be utilized for different size individuals. Additionally, other fastening means can be provided such as Velcro ® hook and eye cloths which is well known in the art.

FIG. 2 is an illustration of a portion 16 of the abdomen 15 of a patient where a belt 11 similar to belt 1 is then placed on the abdomen with a slit 12 corresponding to slit 7 of the belt of FIG. 1 located over the surgical incision and with tube 13 extending through the slit. As shown zipper 14 is provided to close pocket 15 of the device. In the case shown the feeding is being accomplished by means of a syringe 16 adapted to carry a fluid food where the end 18 of of syringe 16 is received on the free end 17 of tube 13 for feeding.

After the feeding is accomplished the tube is then closed off, placed in the pocket 15 and the zipper 14 is closed so that the tube is retained out of the reach of the individual until a subsequent feeding is to be accomplished.

Also the tube is safely stored so that it will not accidentally catch on a toy or other object and be removed from the incision.

It will be understood that the foregoing are but examples of one arrangement within the scope of the present invention and that various other arrangements also within the scope of the present invention will occur to those skilled in the art upon reading the disclosure set forth hereinbefore.

The invention claimed is:

1. A pocket device for retaining a gastronomy tube inserted in the alimentary canal of the patient including an elongated flexible band having spaced first and second sides and opposite ends with cooperative fastener means located at said opposite ends of the band so that the band can be placed and secured around the abdomen of a patient; a pocket member defined between said flexible band and a sheet of flexible material secured in overlying relation with said band around a portion of the periphery thereof at a selected location between the ends of the flexible band wherein said sheet of flexible material includes a first slit and opening and closing means to open and close said slit to provide access to the pocket, and a second slit provided in the band intermediated the ends of the band in general alignment with said first slit so that a gastronomy tube can be received through the slit when the band is secured to the abdomen of a patient and can be stored in the pocket where access to tube can be provided by means of the opening and closing means to allow removal of the free end of the tube of the pocket and replacement.

2. The invention of claim 1 wherein said pocket includes gusset means between said sheet of flexible material and said band to provide selected depth to said pocket.

3. The invention of claim 1 wherein said band contracts and extends in response to change in dimension of the abdomen to which said band is attached.

4. The invention of claim 3 wherein said band includes at least one inset of elastic material along the length thereof to provide the extension and contraction thereof.

5. The invention of claim 3 wherein said band is of elastic material.

6. The invention of claim 1 including elastic strip means secured to at least one of said first and second sides to restrain movement of said band where said band is in place on the abdomen of the user.

7. The invention of claim 1 wherein said first side of said band is shorter than said second side of said band.

* * * * *